United States Patent [19]
Haber et al.

[11] Patent Number: 5,911,848
[45] Date of Patent: Jun. 15, 1999

[54] METHOD FOR MAKING A PUNCTURE EVIDENT DOUBLE LAYER SURGICAL GLOVE

[75] Inventors: Terry M. Haber, El Toro; William H. Smedley, Lake Elsinore; Clark B. Foster, Laguna Niguel, all of Calif.

[73] Assignee: Habley Medical Technology Corporaton, San Diego, Calif.; a part interest

[21] Appl. No.: 08/868,468

[22] Filed: Jun. 3, 1997

[51] Int. Cl.⁶ .............................. B29C 41/14; A41D 19/00
[52] U.S. Cl. .............................. 156/245; 156/292; 2/161.7
[58] Field of Search .................................. 156/245, 292, 156/308.4; 2/161.7

[56] References Cited

U.S. PATENT DOCUMENTS

| | | | |
|---|---|---|---|
| 4,696,065 | 9/1987 | Elenteny | 2/168 |
| 4,881,277 | 11/1989 | Hogle | 2/169 |
| 5,180,605 | 1/1993 | Milner | 427/2 |
| 5,317,760 | 6/1994 | Best | 2/161.7 |
| 5,571,219 | 11/1996 | Gorton | 2/161.7 |
| 5,619,752 | 4/1997 | Haber et al. | 2/161.7 |

*Primary Examiner*—Jeff H. Aftergut
*Assistant Examiner*—Shawn A. Mitchell
*Attorney, Agent, or Firm*—Morland C. Fischer

[57] ABSTRACT

An efficient method for using a single, ceramic hand-shaped mandrel to make an integral double layer surgical glove having an indicator bulb that is adapted to warn a health care worker (e.g. a surgeon) to re-glove in the event that the structural integrity of the glove is compromised as a consequence of a puncture or tear. First and second latex gloves are formed one above the other over the mandrel. An air permeable mold release agent separates the first and second latex gloves and establishes an air channel which lies in communication with the indicator bulb. The indicator bulb, which is responsive to a pressure differential in the air channel, is initially pumped and compressed so as to suction trapped air in the air channel to the atmosphere and thereby create a vacuum. In the event of a puncture or tear through the integral, double layer glove, the indicator bulb will be instantenously filled with air from the atmosphere via the air channel so as to provide a visual warning to the health care worker of such puncture or tear.

20 Claims, 12 Drawing Sheets

METHOD FOR MAKING A PUNCTURE EVIDENT DOUBLE LAYER SURGICAL GLOVE

BACKGROUND OF THE INVENTION

1. Field of the Invention

This invention relates to an efficient method for using a single mandrel to make an integral double layer surgical glove having an indicator bulb that is adapted to warn a health care worker to re-glove in the event that the structural integrity of his glove is compromised by a puncture or tear.

2. Background Art

A rapidly growing problem facing surgeons and health care workers who treat high risk patients is contracting nosocomial infection of hepatitis, AIDS and other contagious diseases through punctured, torn or otherwise structurally compromised surgical gloves. In many instances where a sharp instrument such as a hypodermic needle cannula, scalpel, scissors, and the like, is used in an operating theater, the surgeon will accidentally puncture his glove. This penetration and the unsafe condition resulting therefrom often goes undetected until a surgeon removes his gloves at the end of the operation and discovers a collection of blood inside the glove. Should the patient being treated have a contagious disease, the surgeon will be exposed to the possibility of contracting the disease and to the potentially life-threatening effects thereof. Some surgeons are under the misconception that accidental punctures may be avoided by simply double gloving. However, as a consequence of the very sharp instruments being used in the operating theater, double gloving will offer the surgeon little extra protection against an accidental puncture and the risks inherent therewith.

U.S. patent application Ser. No. 08/628,895 filed Apr. 9, 1996, now U.S. Pat. No. 5,619,752 which is incorporated herein by reference, describes a puncture evident surgical glove having an integral, non-obtrusive indicator bulb by which to accurately, instantaneously and visually alert a health care worker of the need to re-glove as a consequence of a compromise in the structural integrity of his glove as caused by a puncture or a tear. The puncture evident glove includes inner and outer elastomeric (e.g. latex) glove membranes that are spaced from one another to define an air flow path that is hermetically sealed from the atmosphere. An air permeable material fills the space between the membranes to preserve the air flow path therebetween. A flexible indicator bulb having a hollow body is sandwiched between the inner and outer membranes. The indicator bulb communicates with the atmosphere by way of an air exhaust tube. The health care worker will be readily able to determine the status of his glove depending upon whether the indicator bulb is compressed or inflated.

Although there are different methods possible for manufacturing the double layer puncture evident surgical glove described above, what is needed is an efficient, low cost method which is adapted to take advantage of conventional assembly line techniques to enable a large number of such puncture evident surgical gloves to be made in a relatively short time.

SUMMARY OF THE INVENTION

Disclosed below is a method for using a single hand-shaped ceramic mandrel and well known assembly line techniques to manufacture an integral double layer surgical glove having an indicator bulb to warn a health care worker of the need to re-glove in the event that his glove becomes torn or punctured with the result of exposing the health care worker to a possibly contagious and life threatening disease. Initially, a single layer glove is formed by first cleaning the mandrel in a wash tank filled with water and detergent. The mandrel is then moved, as one of a plurality of identical mandrels being carried from station to station by means of a conveyer belt, to a rinse tank where the detergent from the wash tank is removed. After the mandrel is dried in warm air, it is dipped in a first coagulant tank containing water and equal amounts of calcium nitrate and calcium carbonate. From the first coagulant tank, the mandrel is dried in warm air so as to leave the mandrel covered with a powdery mold release agent by which to facilitate the removal of the soon to be described double layer glove. The mandrel is then dipped in a first latex filled tank to cover the mold release agent with a first layer of latex. The mandrel is dried and heated to vulcanize the latex and thereby form a conventional single layer latex glove.

According to the present invention, the mandrel around which the latex glove is disposed is now dipped in a second coagulant tank containing water and about three times more calcium carbonate, by weight, than calcium nitrate. The dip of the mandrel into the second coagulant tank is relatively shallow compared with the dip into the first coagulant tank so that a region around the cuff of the latex glove will not be covered with mold release agent. The mandrel is dried in warm air to leave a more effective mold release agent covering the latex glove, except for the cuff area thereof. Next, the mandrel is dipped in a second latex filled tank so that the first glove, including the cuff area, is now covered with latex. After being dried and heated to vulcanize the second layer of latex, first and second (i.e. inner and outer) latex gloves are formed, one over the other, which are separated by the mold release agent. Inasmuch as the cuff area of the first (i.e. inner) latex glove is not covered with a mold release agent, a latex-to-latex bond is established between the cuff areas of the first and second latex gloves in order to hermetically seal the gloves together. Accordingly, an integral double layer surgical glove is formed over the mandrel with the mold release agent preventing the first and second (i.e. inner and outer) latex gloves from sticking together while, at the same time, establishing a channel around the finger area of the composite glove through which air will flow, after the channel is first evacuated, in the event that the second (i.e. outer) latex glove is punctured or torn. A supply of high pressure air is directed from a series of nozzles that are spaced around the cuff area of the double layer glove. Blasts of air from the nozzles simultaneously inflate and blow the now completed double layer glove off the mandrel into a bin.

A hole is then made through the top of the integral double layer glove near the cuff to receive a hollow, flexible indicator bulb. Upper and lower elastomeric domes are adhesively bonded together and closed against one another at opposite sides of the hole to form the indicator bulb. The bulb is made part of a fluid (i.e. air) path which includes the air channel running between the first and second gloves and the atmosphere. The bulb is initially pumped and compressed so that air within the air channel is evacuated to the atmosphere. A tear or puncture through the double layer glove will place the air channel in communication with the atmosphere, whereby the bulb will be instantaneously inflated via the air channel to send a visual warning signal to the wearer of the need to re-glove.

BRIEF DESCRIPTION OF THE DRAWINGS

According to the present invention.

DESCRIPTION OF THE PREFERRED EMBODIMENT

Figure 1:
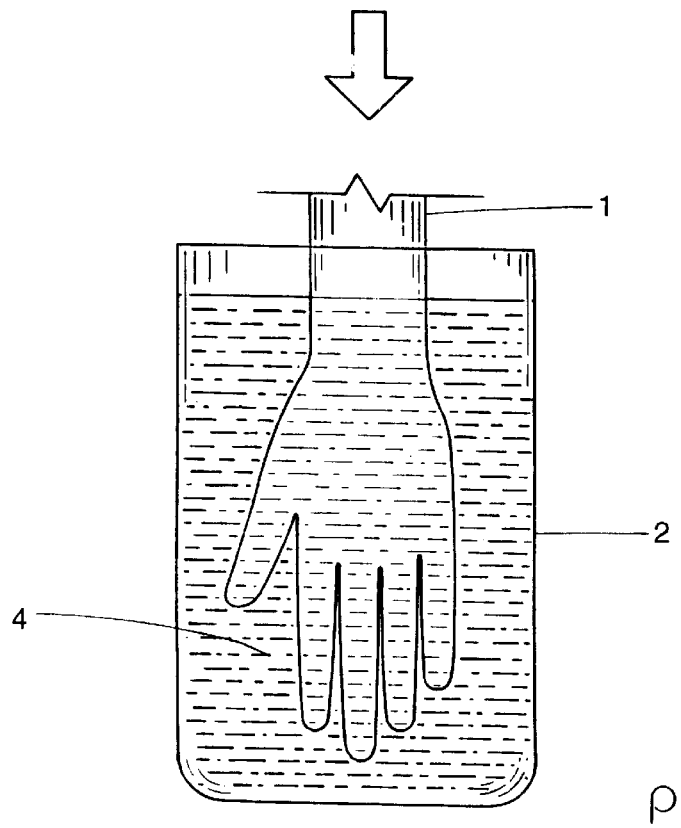
FIGS. 1–8 illustrate the steps for making a conventional single layer latex glove over a ceramic hand-shaped mandrel.
Figure 2:
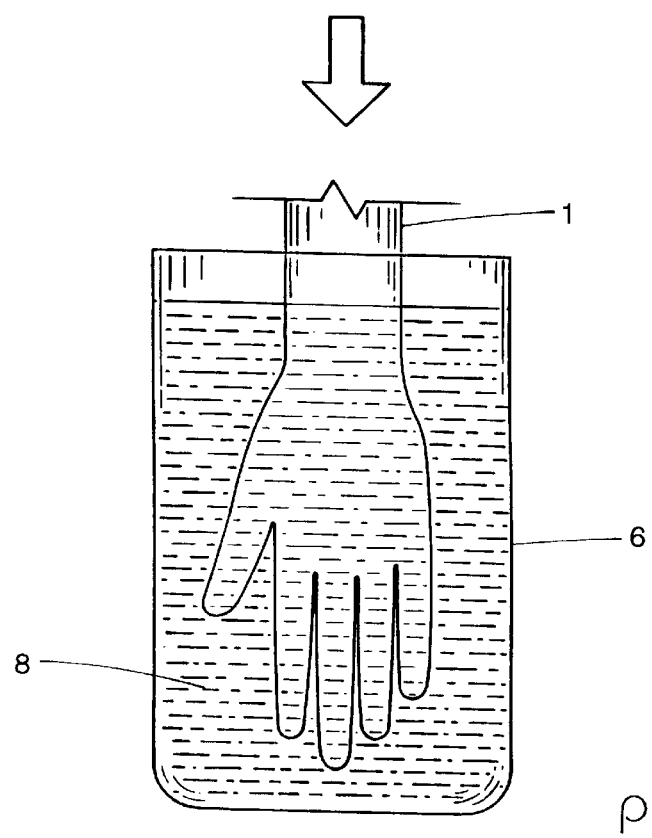
Figure 3:
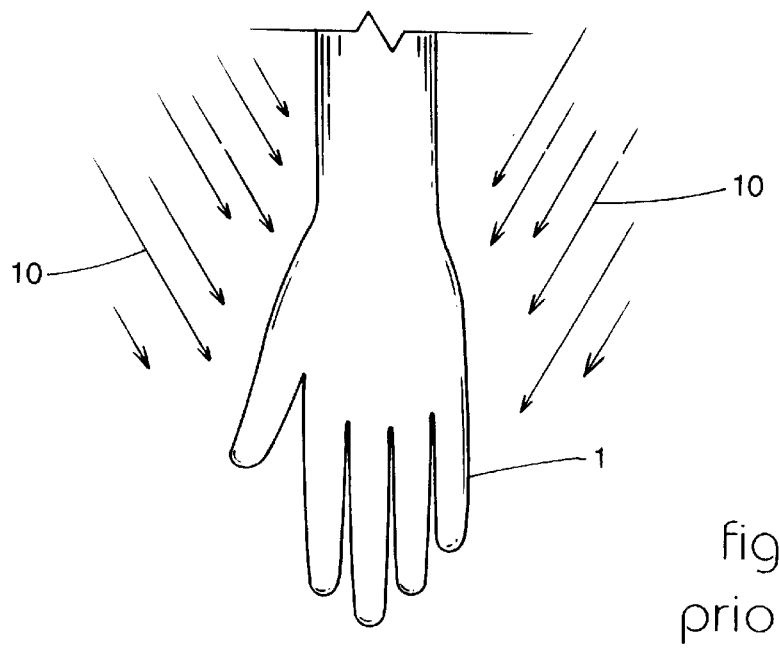

Referring initially to FIGS. 1–8 of the drawings, a conventional method for making a latex glove is described. FIG. 1 shows a ceramic, hand-shaped mandrel 1 which is but one of a number of mandrels that are carried by a conveyer belt (not shown) in assembly-like fashion to be moved from one station to the next. The mandrel 1 is first dipped for a few seconds in a tank 2 that is filled with a solution 4 of water and detergent for the purpose of cleaning the mandrel 1. It may be desirable to constantly rotate the mandrel 1 at this and subsequent stations. Therefore, the mandrel 1 will be uniformly covered with the solution 4 in the cleaning tank 1. The mandrel 1 is withdrawn from the cleaning tank 2 and moved to rinse tank 6 shown in FIG. 2. The rinse tank 6 is filled with clean (e.g. distilled) water 8. The mandrel 1 is once again rotated while it is dipped for a few seconds into the clean water 8 of rinse tank 6 so that the detergent solution 4 of cleaning tank 2 will be removed. The mandrel 1 is now withdrawn from the rinse tank 6 and moved to a drying station of FIG. 3 where warm, dry air 10 is blown over the outside of the mandrel 1 to dry any moisture remaining after its bath in the rinse tank 6 of FIG. 2.

Figure 4:
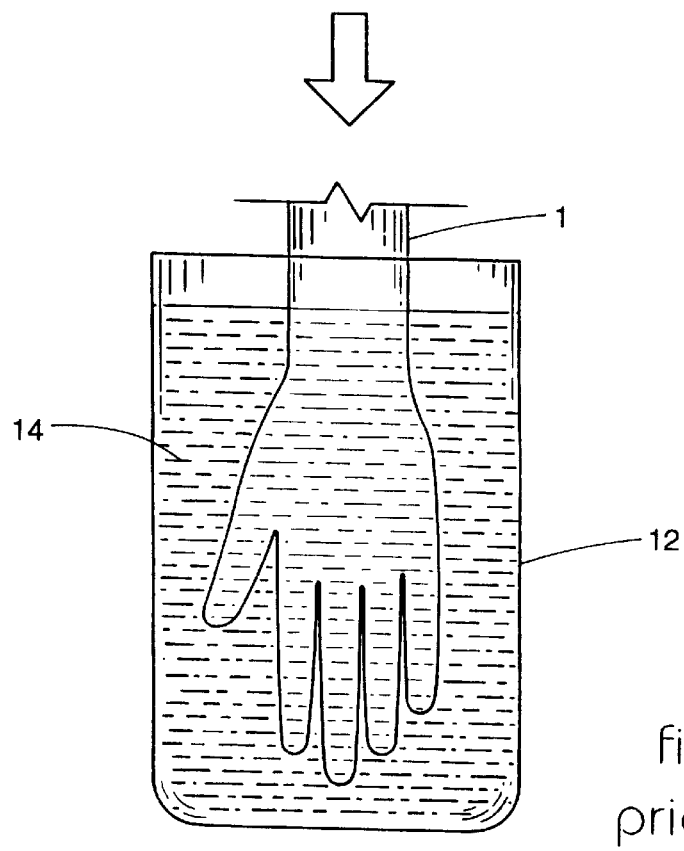

In FIG. 4, the mandrel 1 is dipped in a first coagulant tank 12 that is filled with a solution 14 containing distilled water, calcium nitrate and calcium carbonate. The solution 14 within coagulant tank 12 typically has equal amounts (e.g. approximately 10% by weight) of calcium nitrate and calcium carbonate. The aforementioned compounds are used to cover the mandrel 1 with a jellified coating that, on being dried, will leave a powder residue which acts as a mold release agent 18. The mold release agent 18 is necessary to prevent a soon to be described layer of latex from bonding in close contact with the mandrel 1. In this regard, after the mandrel 1 is withdrawn from the first coagulant tank 12 of FIG. 4, it is moved to another drying station of FIG. 5 where warm, dry air 16 is blown over the outside of the mandrel to drive off any of the water remaining after its bath in the solution 14 of tank 12. After drying, the mandrel 1 is covered with a layer of powder residue which forms a first mold release agent 18.

Figure 5:
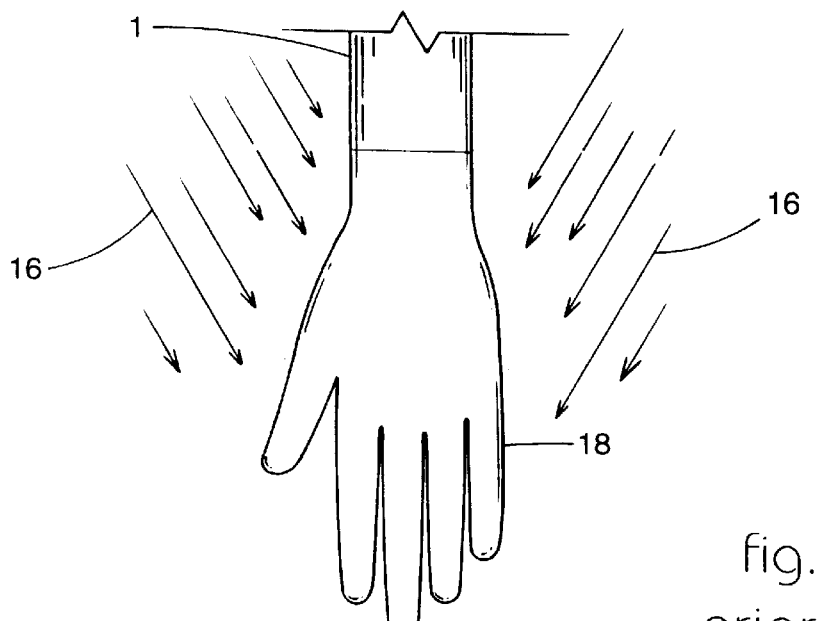
Figure 6:
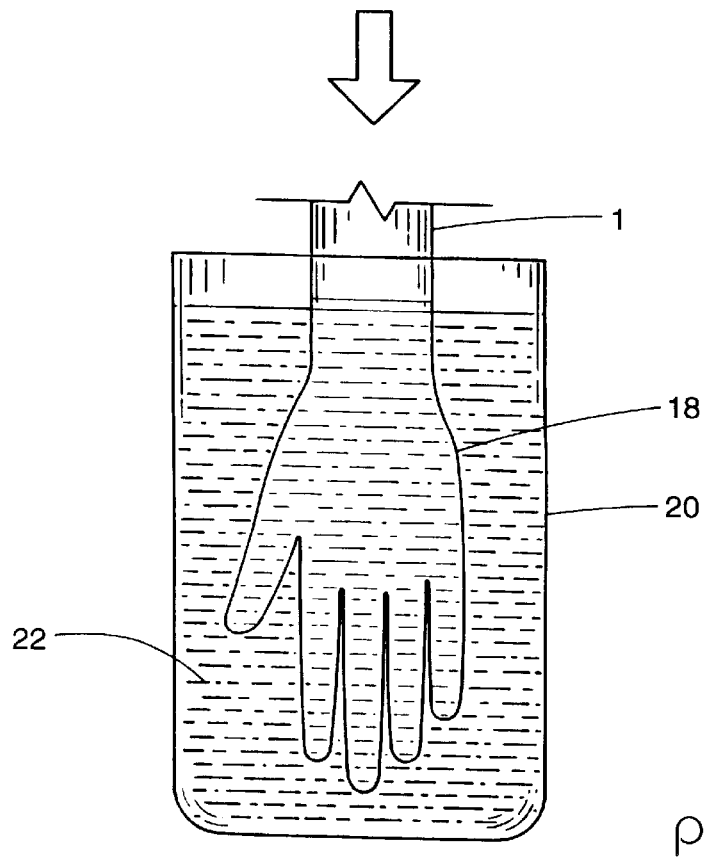
Figure 7:
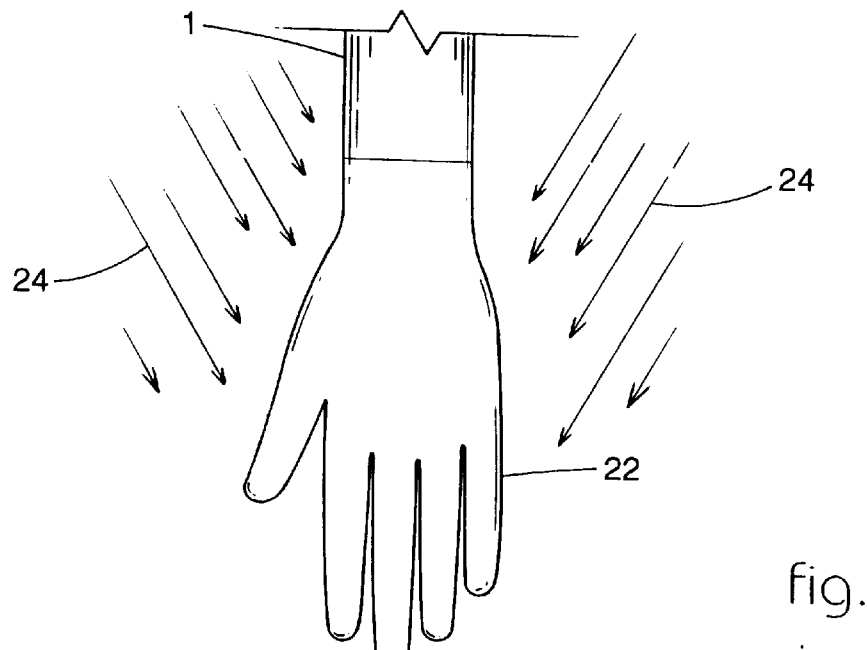
Figure 8:
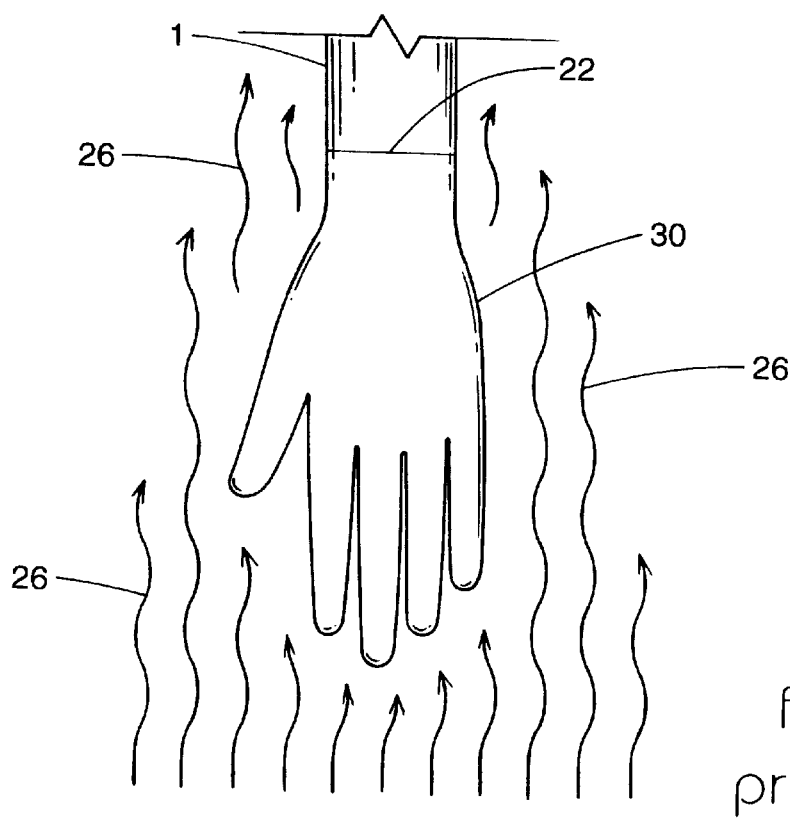

Next, in FIG. 6, the mandrel 1 is moved to a first tank that is filled with an elastomeric material (e.g. latex 22). The mandrel 1 is dipped in the tank 20, whereby the layer of mold release agent 18 of FIG. 5 is now covered with the latex 22. From the first latex filled tank 20 of FIG. 6, the mandrel 1 is moved to another drying station of FIG. 7 and, for about five minutes, warm, dry air 24 is blown over the layer of latex 22 which covers the mold release agent 18 so as to drive off any moisture from the latex. In FIG. 8, the mandrel 1 that has been covered with a first layer of mold release agent 18 and a first layer of latex 22 is subjected to heat 26 that is generated within an oven (e.g. a heat tunnel, or the like). That is, the oven is heated to a temperature of about 250° F., and the mandrel 1 is located therein for a few minutes to vulcanize the latex 22. At this point, a well-known single layer latex glove 30 is formed over the mandrel 1.

FIGS. 9–13 of the drawings show the method of the present invention for making an integral double layer glove (designated 52 in FIG. 13) that is adapted to carry an indicator to warn a user in the event that the glove 52 is punctured, torn, or otherwise violated with the effect of exposing the user to a possibly contagious and life threatening disease. After the steps shown in FIGS. 1–8 are completed and a traditional single layer latex glove 30 is formed, the mandrel 1 is dipped in a second coagulant tank 32 that is filled with a jellified solution 34 containing distilled water, calcium nitrate and calcium carbonate. While the solution 14 within the first latex filled coagulant tank 12 of FIG. 4 contained equal concentrations of calcium nitrate and calcium carbonate, by weight, the solution 34 within the second coagulant tank 32 contains a higher concentration of calcium carbonate, by weight. More particularly, solution 34 contains about 30% calcium carbonate and only 10% calcium nitrate.

The reason for increasing the concentration of calcium carbonate is to advantageously produce a mold release agent that is more effective than the mold release agent 18 that covers the mandrel 1 in FIG. 5. That is, a latex-to-latex bond between the first latex glove 30 and a soon to be described second latex glove will be harder to break than a latex-to-ceramic bond between the first latex glove 30 and the mandrel 1. Therefore, it is desirable that more powder residue (i.e. mold release agent) cover the first latex glove 30 after drying the jellified solution 34 of the second coagulant tank 32 into which the mandrel 1 is dipped in FIG. 9.

Figure 9:
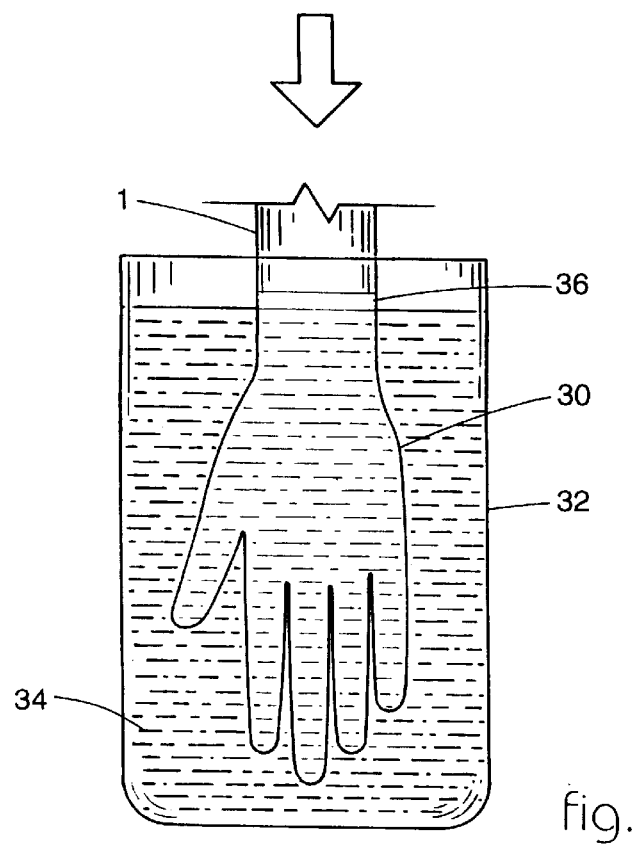
FIG. 9 shows the mandrel over which the first latex glove is formed being dipped into a coagulant tank filled with a mixture of water, calcium carbonate, and calcium nitrate.

In addition, it is also desirable that the second dip of the mandrel 1 into the second coagulant tank 32 of FIG. 9 be relatively shallow compared with the first dip of the mandrel 1 into the first coagulant tank 12 of FIG. 4. The effect of this shallow dip of mandrel 1 into tank 32 is to establish a narrow latex bonding area 36 around the cuff area of the glove 30 where said glove 30 will not be covered with the jellified solution 34 from tank 32 or the powder residue that will remain after solution 34 is dried.

Figure 10:
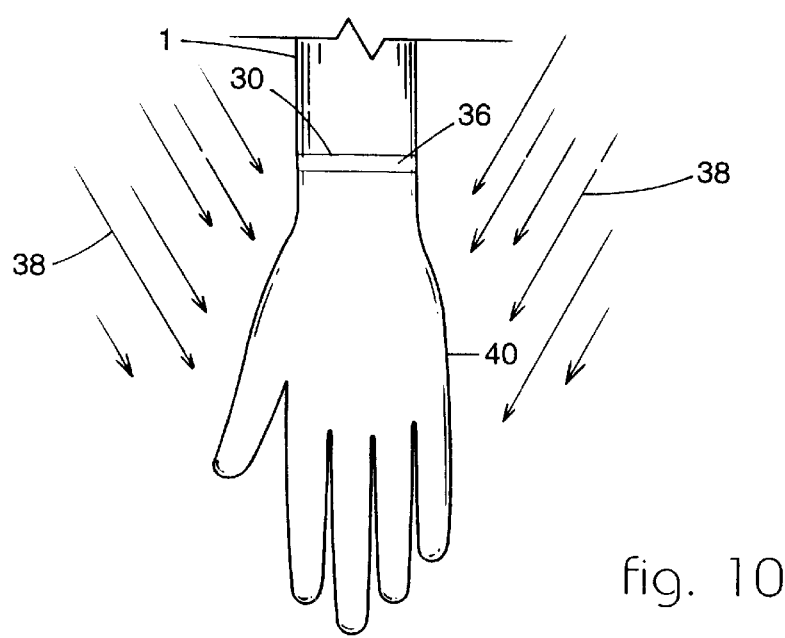
FIG. 10 shows the mandrel being dried so as to leave a residue of mold release agent over the first latex glove.

After the mandrel 1 is withdrawn from the second coagulant tank 32 wherein the first latex glove 30 is coated (except for latex bonding area 36) with the jellified solution 34 including an increased concentration of calcium carbonate, the mandrel is moved to the drying station of FIG. 10. Warm, dry air 38 is blown over the jellified solution 34 which covers the first glove 30 to drive off any water remaining after the bath in the second coagulant tank 32. Once the drying step of FIG. 10 is completed, the first latex glove 30 (except for the latex bonding area 36) will be covered with a second powder layer of mold release agent 40.

Figure 11:
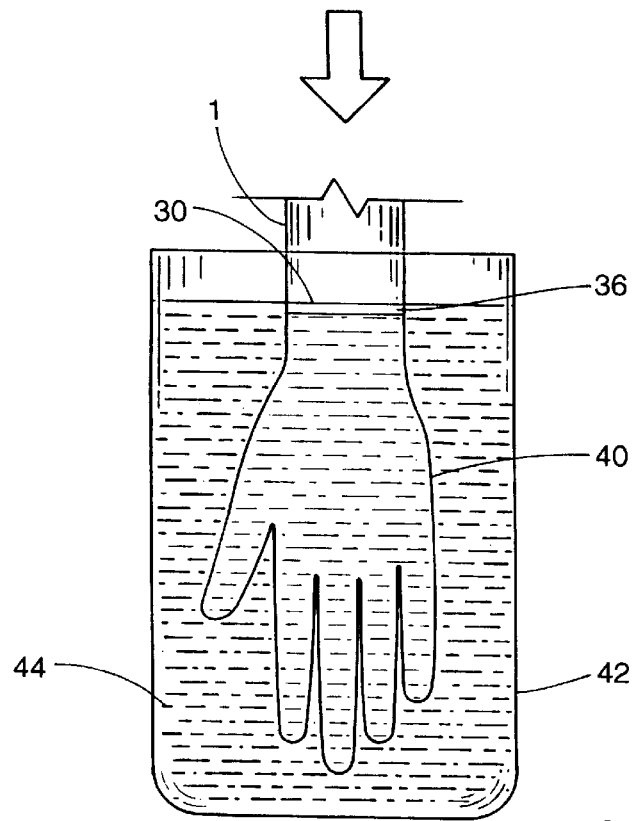
FIG. 11 shows the mandrel being dipped into a latex filled tank to cover the first latex glove with a second layer of latex.

Referring now to FIG. 11, the mandrel 1 is moved to a second tank 42 that is filled with an elastomeric material (e.g. latex 44). The mandrel 1 is dipped for a few seconds into the tank 42, whereby the layer of mold release agent 40 of FIG. 10 is now covered with latex 44. In this case, the mandrel 1 is dipped into tank 42 to the same depth that the mandrel was earlier dipped into the latex filled tank 20 of FIG. 6 so that the latex 44 covers the mold release agent 40 lying over the first latex glove 30 as well as the latex bonding area 36 of glove 30 which is not covered with mold release agent 40. Therefore, a latex-to-latex interface is established at the latex bonding area 36.

Figure 12:
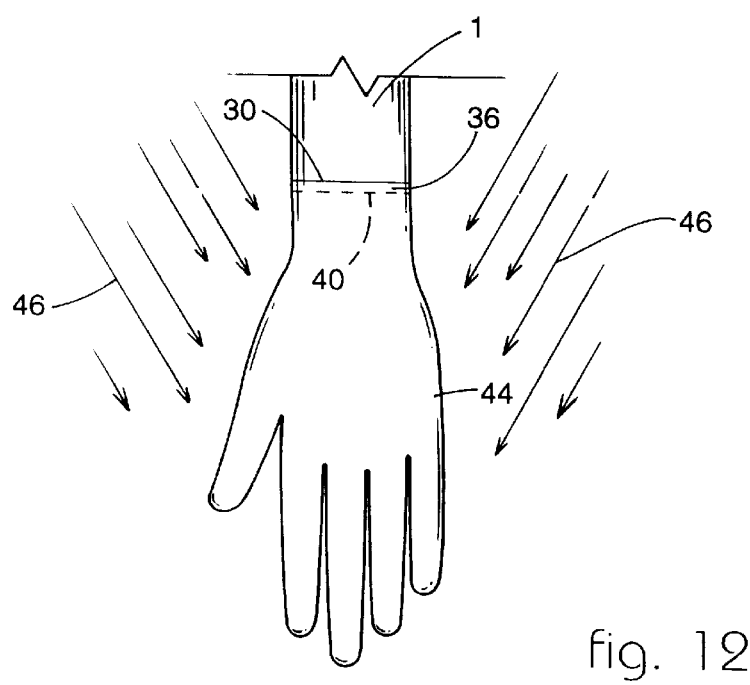
FIGS. 12 and 13 show the second layer of latex being dried and heated, whereby to vulcanize the latex and thereby form a second latex glove covering the first latex glove.

From the second latex filled tank 42 of FIG. 11, the mandrel 1 is moved to a drying station of FIG. 12 and, for about five minutes, warm, dry air 46 is blown over the second layer of latex 44 which covers the mold release agent 40 and the latex bonding area 36 so as to drive off any moisture from the latex.

Figure 13:
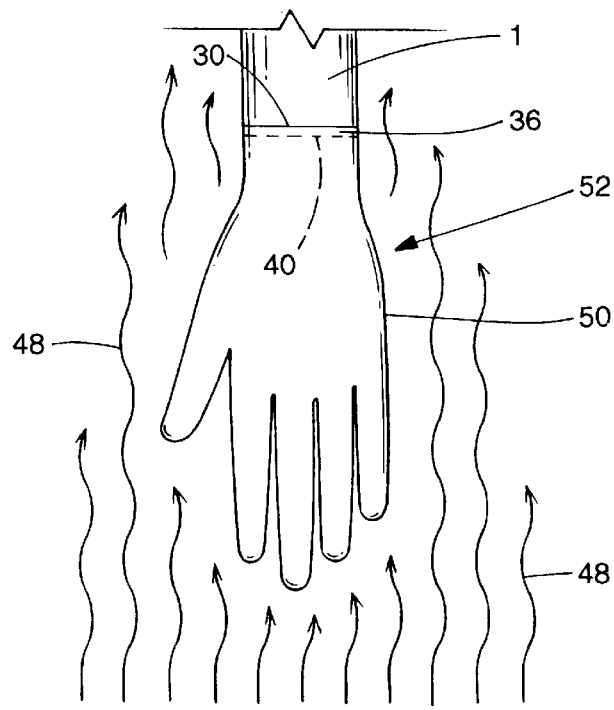

Turning to FIG. 13, the mandrel 1 is now covered by first and second layers of latex 30 and 44 that are separated from one another by the layer of mold release agent 40. The mandrel 1 is now moved to an oven (a heat tunnel) where the second layer of latex 44 is subjected to heat 48 at a temperature of about 250° F. for a few minutes to vulcanize the second layer of latex 44. Accordingly, a second single layer latex glove 50 is formed over the first single layer latex glove 30 with the mold release agent 40 disposed therebetween. At the same time, the heat generated during the vulcanizing step of FIG. 13 causes a latex-to-latex bond to be automatically formed around the latex bonding area 36 at which there is no mold release agent. At this point, a seal is established, whereby to bond the cuff areas of the first and second (i.e. inner and outer) latex gloves 30 and 50 together and thereby form an integral hermetically sealed double layer glove 52.

Figure 14:
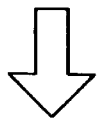
FIGS. 14–16 show an alternate embodiment of the present invention for washing away the mold release agent from between the inner and outer latex gloves where the mold release agent is polyvinyl acetate.
Figure 14:
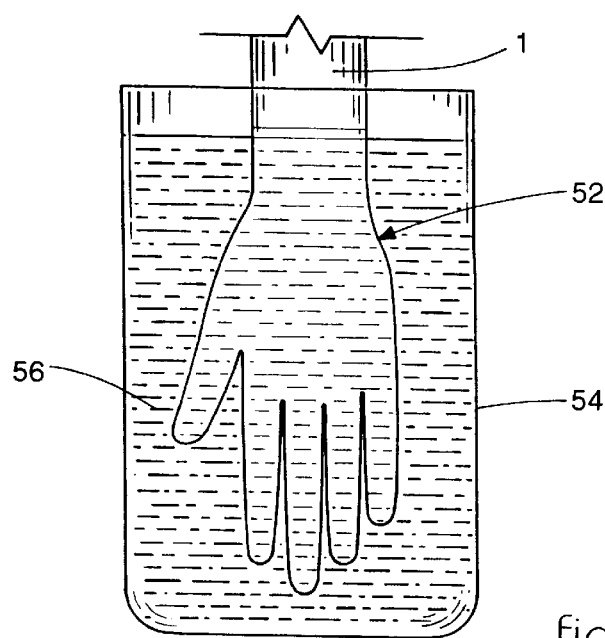
Figure 15:
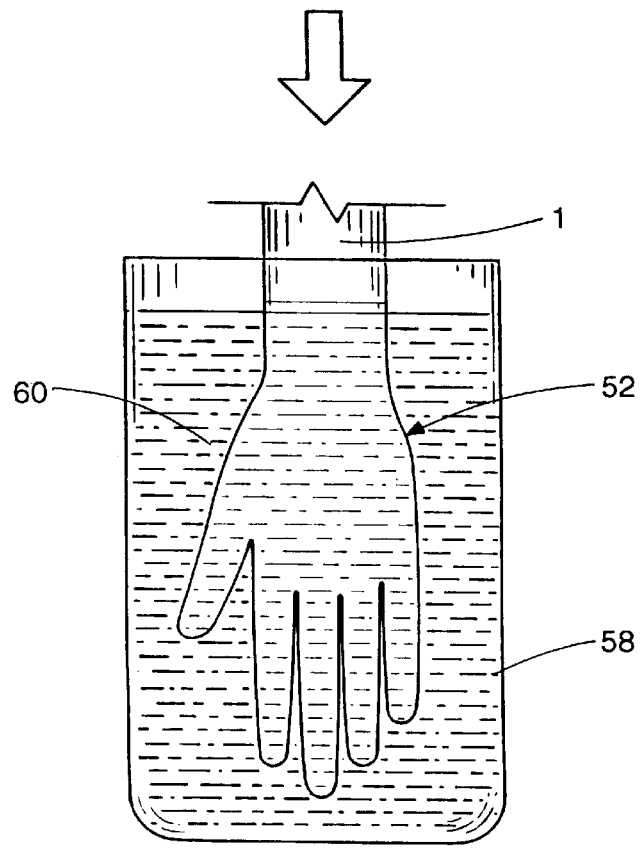
Figure 16:
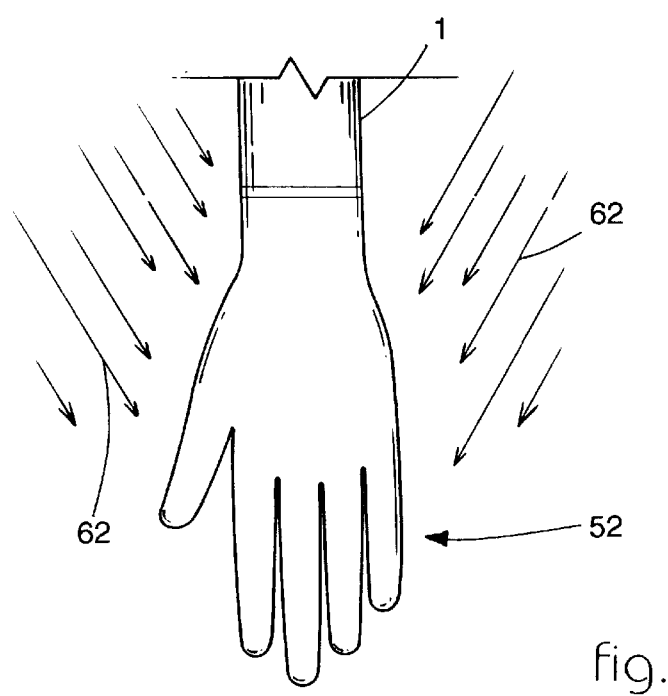

FIGS. 14–16 of the drawings illustrate optional steps of the present invention after the double layer glove 52 is formed by following the steps of FIGS. 1–13. It may be desirable to use a mold release agent other than a solution of water, calcium nitrate and calcium carbonate as described above when referring to FIG. 9. By way of example, the mandrel 1 may be dipped in a coagulant tank (not shown) that is filled with polyvinyl acetate (PVA), or the like, to establish a soluble mold release agent between the inner and outer latex gloves 30 and 50. In this case, the mold release agent may have to be removed from the double layer glove 52.

To this end, FIG. 14 shows the mandrel 1 which carries the double layer glove 52 being dipped in a tank 54 containing a suitable solvent 56 (e.g. water). The top of the glove 52 is punctured to enable the solvent 56 within tank 54 to enter the glove for the purpose of dissolving the PVA between the inner and outer latex gloves 30 and 50. To best dissolve the PVA, it is desirable to subject the double layer glove 52 to an ultrasonic bath within tank 54. The bottom of the glove 52 may also have to be punctured to permit the dissolved PVA to run out of the glove under the influence of gravity.

Once the ultrasonic bath is completed and the PVA dissolved, the double layer glove 52 is removed from tank 54 and moved to a rinse tank 58 of FIG. 15. The rinse tank 58 is filled with clean water to wash the PVA residue from the double layer glove 52. After the washing step of FIG. 15, the glove 52 is removed from the rinse tank 58 and dried in warm air (designated 62 in FIG. 16). In addition, any punctures that are made through the top and bottom of the glove 52 to dissolve and remove the PVA mold release agent are now sealed.

Figure 17:
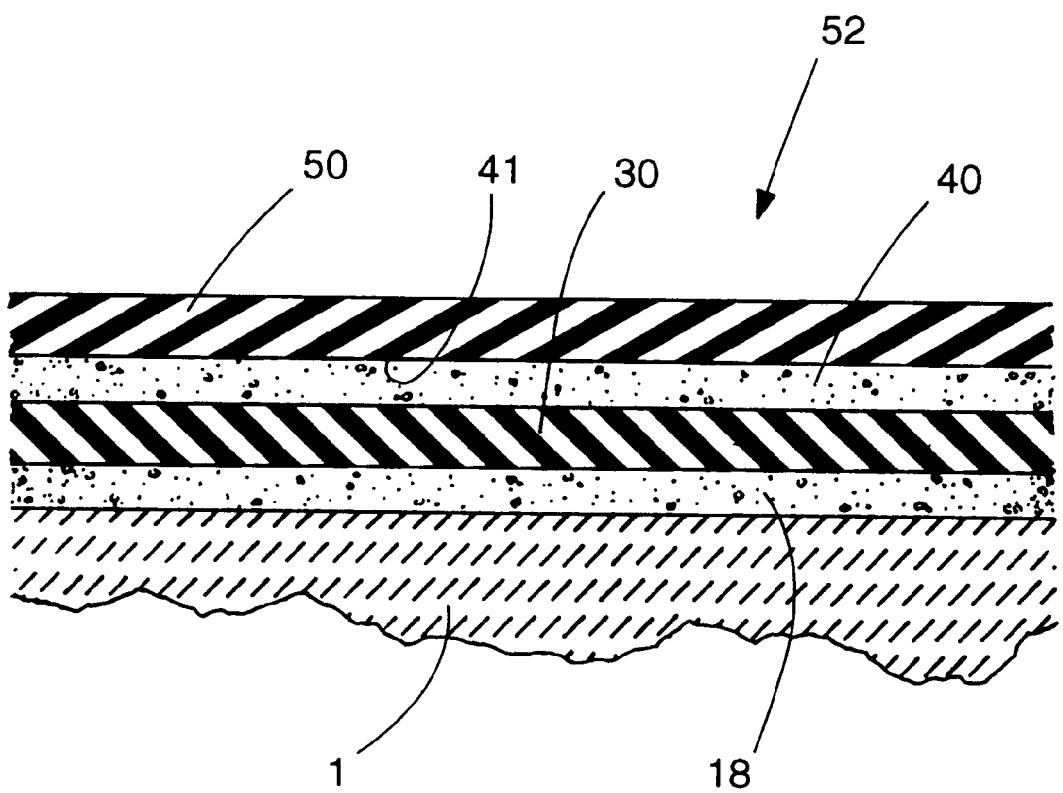
FIG. 17 is a partial cross section of the now completed integral double layer glove showing the first and second latex gloves, spaced one above the other, after the method steps of FIGS. 1–13 have been completed.

FIG. 17 shows a partial cross section of the integral double layer glove 52 which surrounds the ceramic mandrel 1 at the conclusion of the method steps illustrated in FIGS. 1–13. More particularly, the mandrel 1 is covered with a first mold release agent 18, and a first (i.e. inner) latex glove 30 covers the mold release agent 18. As will be described when referring to FIG. 18, the first mold release agent 18 between the first latex glove 30 and the mandrel 1 facilitates the removal of the double layer glove 52 from the mandrel.

A second mold release agent 40 is left between the first and second (i.e. inner and outer) latex gloves 30 and 50 of the double layer glove 52. The second mold release agent 40 is air permeable so as to prevent the first and second latex gloves from sticking together while, at the same time, establishing a channel 41 that runs between the gloves 30 and 50 and around the finger area of the double layer glove 52. After first being evacuated, air from the atmosphere will flow through channel 41 in the event that the second (i.e. outer) glove 50 is punctured or torn (as disclosed in co-pending Patent Application No. 08/628,895). That is to say, the double layer glove 52 is made responsive to a pressure differential to alert a user as to the need to re-glove.

Figure 18:
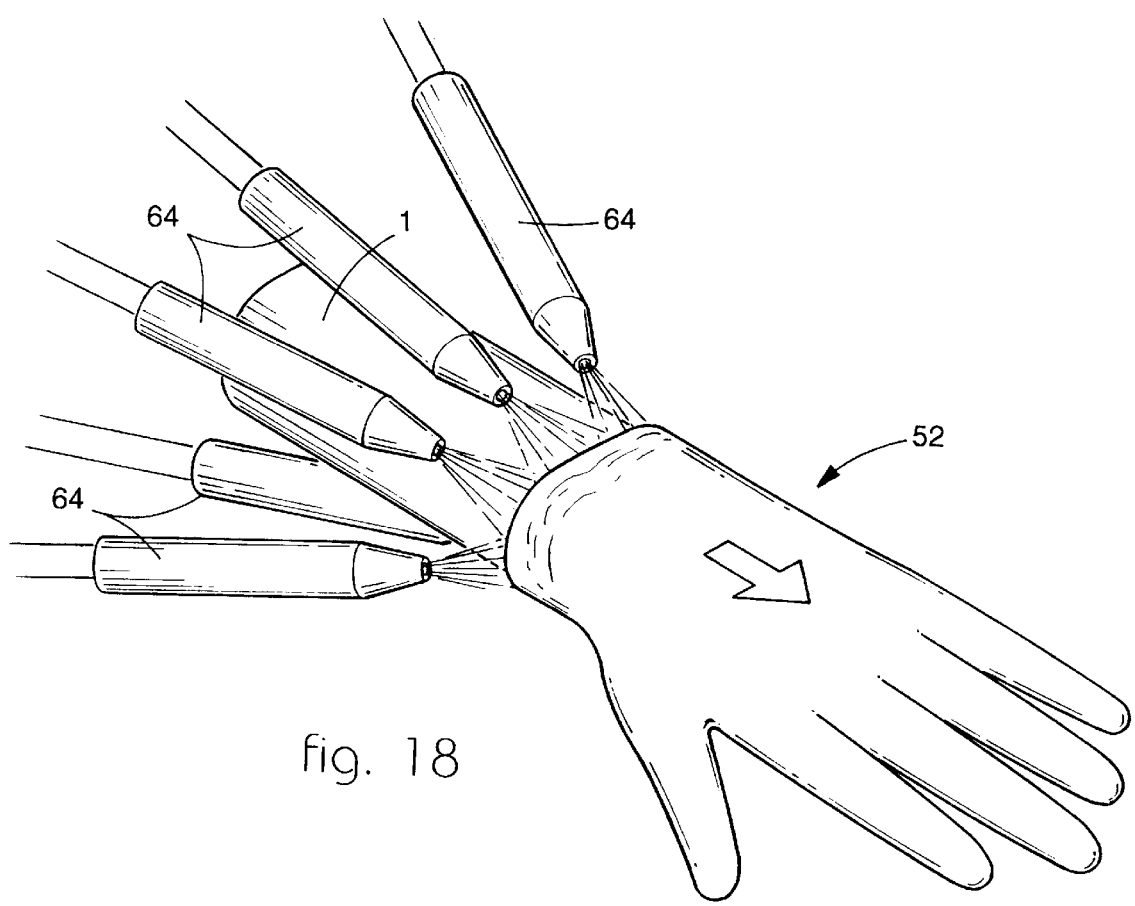
FIG. 18 shows the double layer glove being blown off the mandrel.
Figure 21:
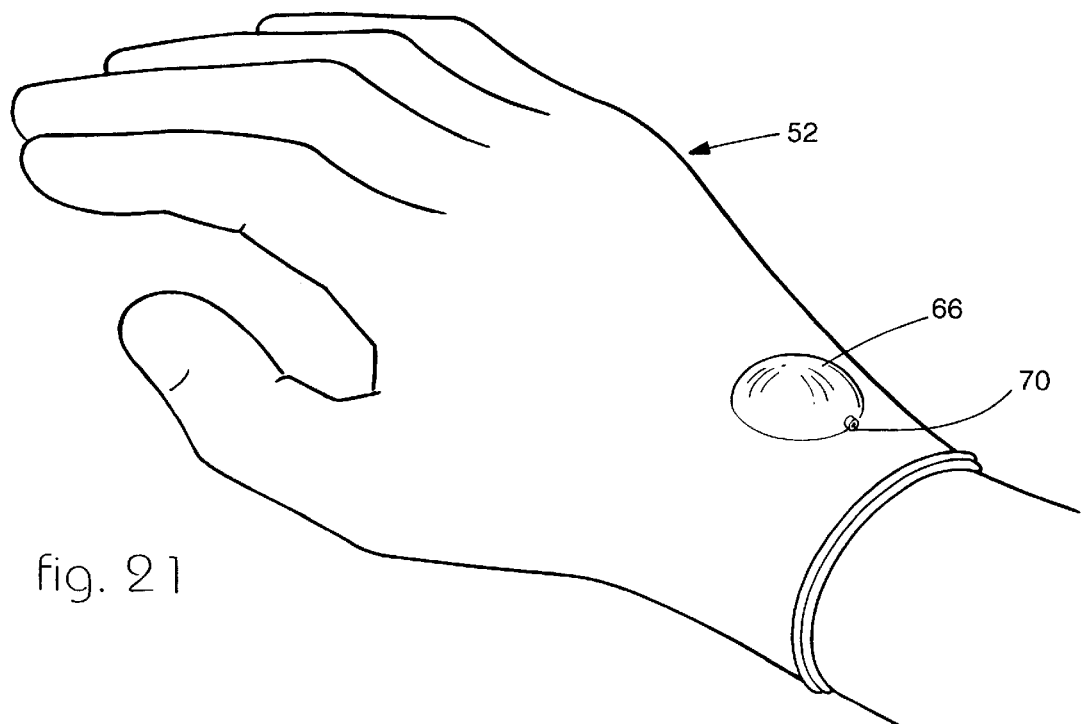
FIGS. 20 and 21 illustrate the operation of the indicator bulb with the integral double layer glove to provide an instantaneous and visual warning in the event that the structural integrity of the double layer glove should be compromised as a consequence of a puncture or tear.
Figure 20:
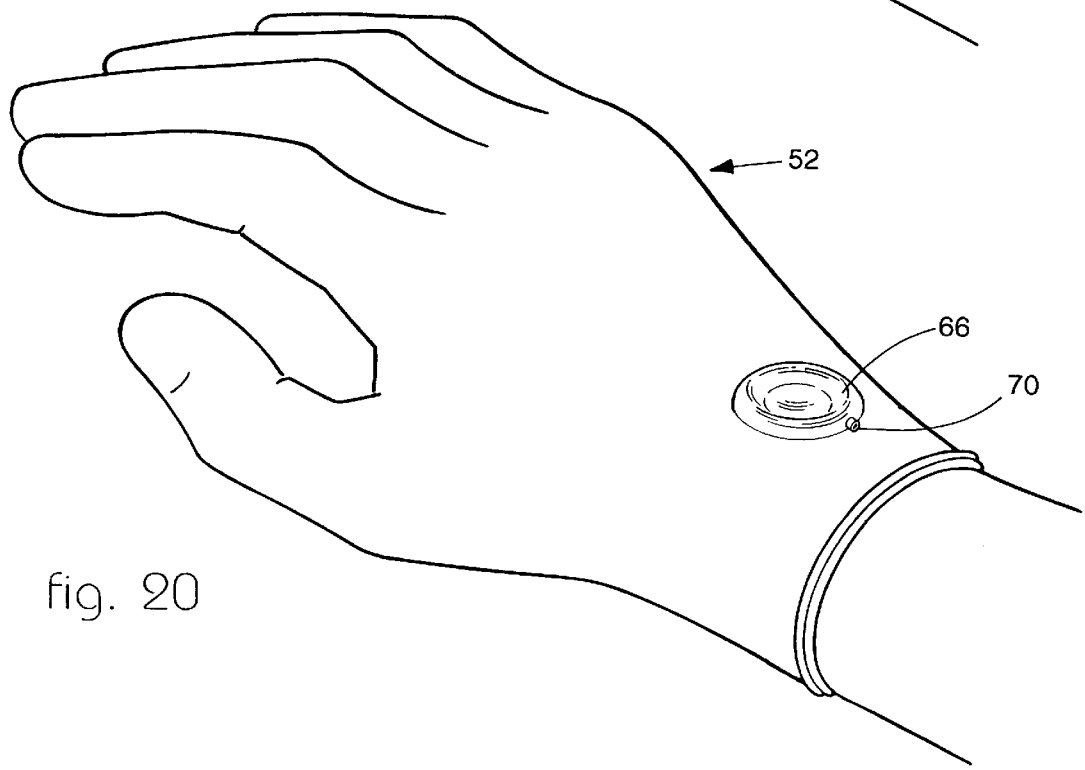

FIG. 18 of the drawings shows a supply of high pressure air being used to strip the integral double layer glove 52 from the mandrel 1 so that the glove 52 will be ready to receive a puncture indicator (designated 66 in FIG. 20 and 21). A plurality of air nozzles 64 are uniformly spaced around the mandrel 1 upon which the glove 52 is seated. The air nozzles 64 are aligned to direct high pressure blasts of air from a source thereof between the mandrel 1 and the first (i.e. inner) glove 30. By virtue of the first mold release agent 18 lying between the mandrel 1 and the first latex glove 30, the air blasts from nozzle 64 act to simultaneously inflate and blow the double layer glove 52 off the mandrel 1. The newly formed integral double layer glove 52 is caught in a suitable bin and moved to a station so that an indicator (i.e. like that disclosed in copending patent application Ser. No. 08/628,895) may now be installed.

Figure 19:
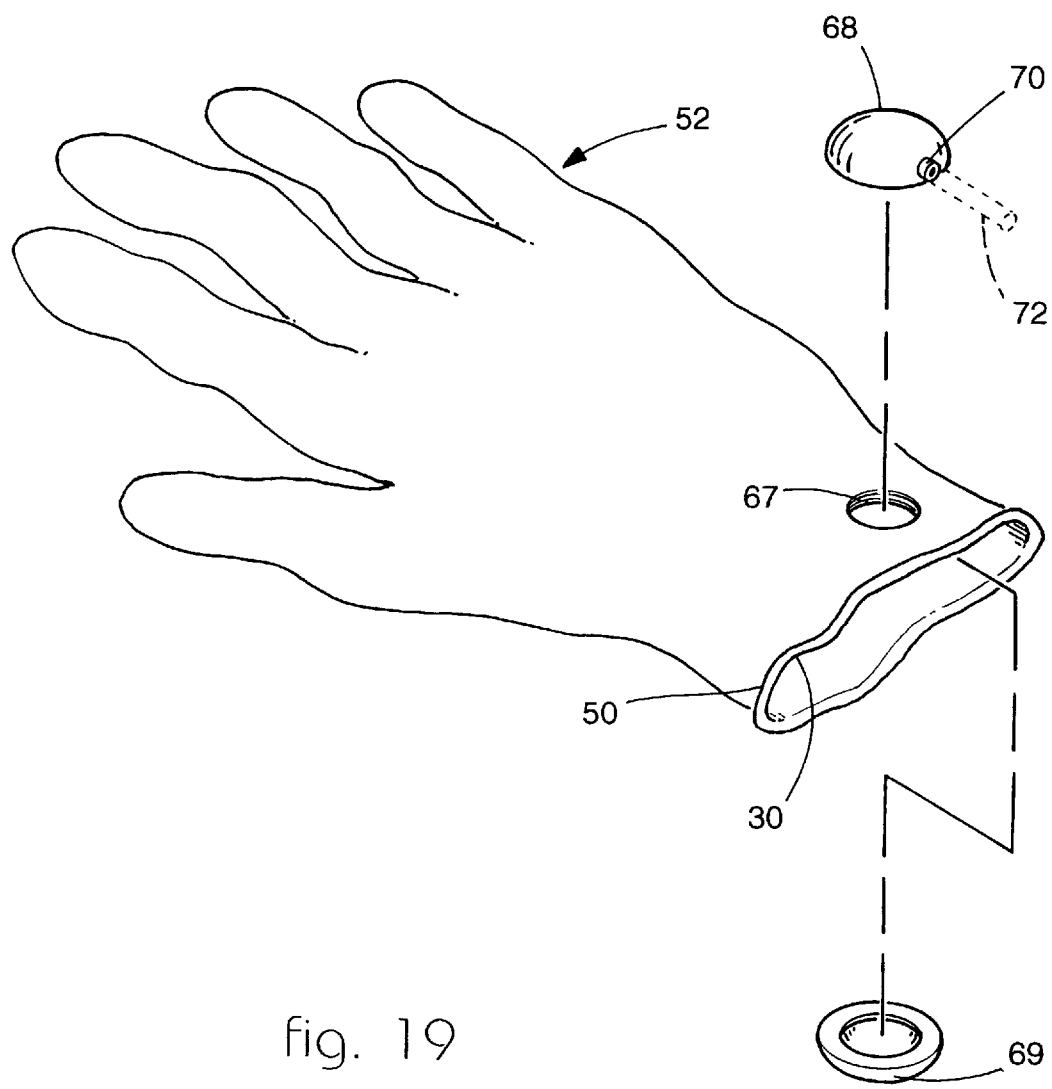
FIG. 19 shows an elastomeric indicator bulb being assembled in the double layer glove.

FIGS. 19–21 of the drawings illustrate the step of securing a hollow, flexible indicator bulb (designated 66 in FIGS. 20 and 21) to the composite double layer glove 52 so as to provide a warning to the wearer of a tear or puncture in the glove and the need to re-glove. First, a hole 67 is cut through the top of the glove 52 near the cuff area. A pair of elastomeric (e.g. latex) domes 68 and 69 are then adhesively bonded together and closed against one another at opposite sides of the hole 67 by means of a suitable rubber glue so that the indicator bulb 66 communicates with the channel 41 (of FIG. 17) that runs between the first and second gloves 30 and 50 and around the finger area of the composite glove 52. One of the elastomeric domes 68 contains a normally closed exhaust tube port 70 to receive an evacuation needle 72 (shown in phantom lines in FIG. 19) that extends between the indicator bulb 66 and the atmosphere. The evacuation needle 72 is installed at the factory to momentarily open the exhaust tube port 70 in order to draw a vacuum within the channel 41. The exhaust tube port 70 and evacuation needle 72 may be replaced by any suitable one way air vent through which air can be exhausted to the atmosphere.

More particularly, the flexible indicator bulb 66 is initially pumped prior to the composite double layer glove 52 being packaged so that air trapped within channel 41 is suctioned to the atmosphere through the evacuation needle 72 that is to be attached to the exhaust tube port 70 following manufacture of the glove 52. When the indicator bulb is finally compressed, the evacuation needle 72 is removed from exhaust tube port 70, whereby the port 70 is automatically closed so as to isolate bulb 66 from the atmosphere. The composite double layer glove 52 having the indicator bulb 66 remaining in the compressed condition is now ready to be shipped in a sterile air-evacuated package.

In the event of a tear or puncture through the double layer glove 52 and a compromise in the structural integrity thereof at any time prior to or during use, the channel 41 will be placed in communication with the atmosphere. In this case and as best shown in FIG. 21, the bulb 66 will be automatically inflated with air that flows through channel 41 so as to provide an immediate visual warning to the wearer of the need to select a new glove so as to avoid the possibility of contracting a contagious and potentially life threatening disease.

It will be apparent that while a preferred embodiment of the invention has been shown and described, various modifications and changes may be made without departing from the true spirit and scope thereof. For example, while the method described above is directed specifically to a double layer surgical glove, it is to be understood that this invention is also applicable to making other gloves having outer and inner layers of latex and an air flow channel running therebetween so as to possess the ability to immediately and visually warn of a puncture or tear and a corresponding compromise in the structural integrity thereof.

We claim:

1. A method for making an integral double layer glove having means to provide a warning in the event of a puncture or tear in said glove, said method comprising the steps of:
    supplying a first latex glove having a cuff area and locating said first latex glove over a hand-shaped mandrel;
    applying a mold release agent over said first latex glove;
    covering said mold release agent with liquid latex;
    curing said liquid latex to form a second latex glove having a cuff area, said second latex glove being located over and spaced from said first latex glove with said mold release agent sandwiched in a space that is established therebetween;
    bonding the respective cuff areas of said first and second latex gloves together so as to form said integral double layer glove;
    removing said integral double layer glove from the mandrel;
    attaching to said integral double layer glove a hollow flexible bulb that communicates with the space between said first and second latex gloves so as to be responsive to a puncture or tear in said double layer glove and adapted to provide a warning thereof; and
    forming said hollow flexible bulb by cutting a hole through the first and second latex gloves of said integral double layer glove and joining first and second elastomeric domes together at opposite sides of said glove through which said hole is cut.

2. The method recited in claim 1, including the additional steps of forming said mold release agent to be applied over said first latex glove from an aqueous mixture containing water, calcium carbonate and calcium nitrate; and heating said aqueous mixture to remove the water and dry said mold release agent to a solid.

3. The method recited in claim 2, including the additional step of forming said mold release agent with a concentration of approximately three times more calcium carbonate, by weight, than calcium nitrate.

4. The method recited in claim 1, including the additional step of forming said mold release agent to be applied over said first latex glove from polyvinyl acetate.

5. The method recited in claim 4, including the additional steps of dissolving said polyvinyl acetate mold release agent from between said first and second latex gloves of said integral double layer glove and removing the dissolved polyvinyl acetate from said double layer glove.

6. The method recited in claim 5, including the additional step of puncturing said integral double layer glove so that a solvent for dissolving said polyvinyl acetate mold release agent from between said first and second latex gloves can be supplied to and drained from said integral double layer glove.

7. The method recited in claim 6, including the additional step of dissolving said polyvinyl acetate mold release agent from between said first and second latex gloves by dipping said integral double layer glove in an ultrasonic solvent bath.

8. The method recited in claim 1, including the additional steps of applying said mold release agent over said first latex glove except for the cuff area of said first latex glove; and
    covering said mold release agent and the cuff area of said first latex glove with said liquid latex to form a latex-to-latex bonding region between said liquid latex and the cuff area of said first latex glove.

9. The method recited in claim 8, including the additional step of heating said liquid latex covering said mold release agent for curing said liquid latex and forming said second latex glove and for thermally bonding the respective cuff areas of said first and second latex gloves together at said latex-to-latex bonding region.

10. The method recited in claim 1, including the additional step of supplying bursts of air, under pressure, to remove said integral double layer glove from the mandrel.

11. The method recited in claim 1, including the additional step of pumping said hollow flexible bulb so as to suction trapped air in the space between said first and second latex gloves to the atmosphere for creating a vacuum within said space.

12. The method recited in claim 1, wherein said first latex glove is located over the hand-shaped mandrel by first dipping the mandrel in liquid latex and then curing said liquid latex.

13. A method for making an integral double layer glove having means to provide a warning of a puncture or tear in said glove, said method comprising the steps of:
    supplying a first latex glove over a hand-shaped mandrel, said first latex glove having a cuff area;
    forming a second latex glove over said first latex glove so that a space is created between said first and second latex gloves, said second latex glove having a cuff area;
    locating an air permeable material within the space between said first and second latex gloves so as to separate said first and second latex gloves from one another and establish an air channel;
    bonding the respective cuff areas of said first and second latex gloves together to form said integral double layer glove;
    removing said integral double layer glove from said mandrel;

attaching to said integral double layer glove flexible pressure responsive indicator means that communicates with said air channel in the space between said first and second latex gloves and is adapted to expand from a compressed state to an inflated state to provide a warning in the event of a puncture or tear in said integral double layer glove and a pressure change within said air channel; and pumping said flexible pressure responsive indicator means for suctioning to the atmosphere air from said air channel in the space between said first and second latex gloves of said double layer glove until said indicator means remains in the compressed state after air is evacuated therefrom.

14. The method recited in claim 13, including the additional steps of opening an air vent in communication with said flexible pressure responsive indicator means through which air from said space between said first and second latex gloves of said double layer glove is suctioned to the atmosphere when said indicator means is compressed, and closing said air vent when said indicator means remains in the compressed state.

15. The method recited in claim 13, including the additional steps of forming said flexible pressure responsive indicator means by cutting a hole through the second latex glove of said integral double layer glove to communicate with said space between said first and second latex gloves, and affixing to said second latex glove a hollow elastomeric dome that communicates with said space via said hole.

16. The method recited in claim 13, including the additional steps of applying a mold release agent over said first latex glove except for the cuff area of said first latex glove; and covering said mold release agent and the cuff area of said first latex glove with a liquid latex to form a latex-to-latex bonding region between said liquid latex and the cuff area of said first latex glove.

17. The method recited in claim 16, including the additional step of heating said liquid latex covering said mold release agent for curing said liquid latex and forming said second latex glove and for thermally bonding the respective cuff areas of said first and second latex gloves together at said latex-to-latex bonding region.

18. The method recited in claim 16, including the additional steps of forming said mold release agent to be applied over said first latex glove from polyvinyl acetate, and removing said polyvinyl acetate mold release agent from said glove.

19. The method recited in claim 13, including the additional step of supplying bursts of air pressurized to remove said integral double layer glove from the mandrel.

20. A method for making an integral double layer glove having means to provide a warning in the event of a puncture or tear in said glove, said method comprising the steps of:

supplying a first latex glove having a cuff area and locating said first latex glove over a hand-shaped mandrel;

applying a polyvinyl acetate mold release agent over said first latex glove;

covering said mold release agent with liquid latex;

curing said liquid latex to form a second latex glove having a cuff area, said second latex glove being located over and spaced from said first latex glove with said mold release agent sandwiched in a space that is established therebetween;

bonding the respective cuff areas of said first and second latex gloves together so as to form said integral double layer glove;

dissolving said polyvinyl acetate mold release agent from between said first and second latex gloves of said integral double layer glove and removing the dissolved polyvinyl acetate from said double layer glove;

removing said integral double layer glove from the mandrel; and attaching to said integral double layer glove indicator means that is responsive to a puncture or tear in said double layer glove and adapted to provide a warning thereof.

* * * * *